United States Patent
Park et al.

(10) Patent No.: US 11,865,514 B2
(45) Date of Patent: Jan. 9, 2024

(54) CATALYST FOR PRODUCING OLEFIN, INCLUDING OXYGEN CARRIER MATERIAL AND DEHYDROGENATION CATALYST

(71) Applicants: SK GAS CO., LTD., Seongnam-si (KR); KOREA RESEARCH INSTITUTE OF CHEMICAL TECHNOLOGY, Daejeon (KR)

(72) Inventors: Yong Ki Park, Seoul (KR); Won Choon Choi, Daejeon (KR); Daesung Park, Daejeon (KR); Hawon Park, Daejeon (KR); Changyeol Song, Daejeon (KR); Deuk Soo Park, Yongin-si (KR); Ung Gi Hong, Seongnam-si (KR); Miyoung Lee, Seoul (KR)

(73) Assignees: SK GAS CO., LTD., Seongnam-si (KR); KOREA RESEARCH INSTITUTE OF CHEMICAL TECHNOLOGY, Daejeon (KR)

(*) Notice: Subject to any disclaimer, the term of this patent is extended or adjusted under 35 U.S.C. 154(b) by 373 days.

(21) Appl. No.: 17/281,114

(22) PCT Filed: May 14, 2019

(86) PCT No.: PCT/KR2019/005548
§ 371 (c)(1),
(2) Date: Mar. 29, 2021

(87) PCT Pub. No.: WO2020/138600
PCT Pub. Date: Jul. 2, 2020

(65) Prior Publication Data
US 2021/0354113 A1   Nov. 18, 2021

(30) Foreign Application Priority Data
Dec. 28, 2018 (KR) .................. 10-2018-0172282

(51) Int. Cl.
*B01J 23/26* (2006.01)
*B01J 21/04* (2006.01)
(Continued)

(52) U.S. Cl.
CPC ............... *B01J 23/26* (2013.01); *B01J 21/04* (2013.01); *B01J 23/30* (2013.01); *B01J 23/34* (2013.01);
(Continued)

(58) Field of Classification Search
CPC ... B01J 23/26; B01J 21/04; B01J 23/30; B01J 23/34; C07C 5/48
See application file for complete search history.

(56) References Cited

U.S. PATENT DOCUMENTS 3,960,975 A    6/1976 Manning
2017/0313637 A1  11/2017 Sofranko et al.

FOREIGN PATENT DOCUMENTS

KR   10-2017-0077959 A   7/2017
KR   10-2018-0078540 A   7/2018

OTHER PUBLICATIONS

International Search Report for PCT/KR2019/005548 dated Sep. 25, 2019 from Korean Intellectual Property Office.
(Continued)

*Primary Examiner* — James A Fiorito
(74) *Attorney, Agent, or Firm* — Paratus Law Group, PLLC (57) ABSTRACT

Disclosed is a catalyst for producing an olefin including an oxygen carrier material and a dehydrogenation catalyst. The catalyst allows hydrogen to be converted into water by using oxygen inside the lattice of an oxide catalyst without the additional supply of oxygen, and thus, the conversion can be increased while the decrease in selectivity, which is a
(Continued)

disadvantage of an additional oxidative dehydrogenation reaction (ODHP), is suppressed.

1 Claim, 7 Drawing Sheets (51) Int. Cl.
*B01J 23/30* (2006.01)
*B01J 23/34* (2006.01)
*C07C 5/48* (2006.01)

(52) U.S. Cl.
CPC ............ *C07C 5/48* (2013.01); *C07C 2521/04* (2013.01); *C07C 2523/26* (2013.01)

(56) References Cited

OTHER PUBLICATIONS

Ryan B. Dudek et al., "Manganese-Containing Redox Catalysts for Selective Hydrogen Combustion Under a Cyclic Redox Scheme", AIChE Journal, Apr. 16, 2018, pp. 3141-3150, vol. 64, No. 8.

CATALYST FOR PRODUCING OLEFIN, INCLUDING OXYGEN CARRIER MATERIAL AND DEHYDROGENATION CATALYST

CROSS-REFERENCE TO PRIOR APPLICATIONS

This application is a National Stage Patent Application of PCT International Patent Application No. PCT/KR2019/005548 (filed on May 14, 2019) under 35 U.S.C. § 371, which claims priority to Korean Patent Application No. 10-2018-0172282 (filed on Dec. 28, 2018), which are all hereby incorporated by reference in their entirety.

BACKGROUND

The present invention relates to a catalyst for producing an olefin with improved selectivity and conversion, including an oxygen carrier material.

Olefins such as ethylene and propylene have been widely used in the petrochemical industry. In general, these olefins are obtained by a naphtha thermal cracking process. However, since the petrochemical industry requires larger amounts of olefins, olefins are also produced via a dehydrogenation process of lower hydrocarbons using catalysts.

All existing propane dehydrogenation (PDH) commercial processes use fixed bed reactors.

In contrast, fluidized propane dehydrogenation (FPDH) using a fluidized bed reactor has not been commercialized to date.

The biggest difference between the fixed bed reactor and the fluidized bed reactor is the contact time between a catalyst and a reactant (propane). That is, the FPDH is a process in which propane and a catalyst are injected together into a fluidized bed reactor at a very high rate to react the propane and the catalyst, and then the catalyst enters a regeneration part and a product enters a separation part.

A goal of a conventionally developed FPDH process is to reduce the residence time of a catalyst to 10 seconds or less. Since the residence time of the catalyst is short, the injection rate of the amount of propane supply is correspondingly fast, and the catalyst is immediately regenerated and participates in the reaction again, the amount of propylene produced when the FPDH process is developed as a commercial process is increased significantly compared to the fixed bed process.

However, the efficiency of the catalyst becomes very important because the contact time between the catalyst and propane is so short. That is, it is important to maximize the selectivity and conversion, which are two measures of efficiency of the catalyst.

Furthermore, the propane dehydrogenation process technologies currently used are constituted based on a noble metal catalyst or a discontinuous process, and there is a problem with the operation of a catalyst bed even in a continuous process, so that the technologies are not suitable for mass production of propylene on the scale of several million tons Further, the propane dehydrogenation reaction has a thermodynamic limitation on the propane conversion due to the reversible reaction between propylene and hydrogen, which are produced. Accordingly, in order to effectively mass-produce propylene, there is a need for developing a new propane dehydrogenation process with reduced production costs by solving the problems of the continuous process and using an inexpensive non-noble metal catalyst in which the selectivity and the conversion are maximized.

In the case of a noble metal catalyst among catalysts used for propane dehydrogenation, the reaction proceeds by a direct dehydrogenation mechanism in which hydrogen is adsorbed on an active site, but in the case of transition metal oxides, the mechanism has not been clearly elucidated due to the incompleteness of the active site caused by electron mobility.

Under these circumstances, the catalysts most commonly used as PDH catalysts are Pt, Pt—Sn, VOx, and CrOx catalysts, and the CrOx catalyst is extremely excellent in terms of propane conversion and propylene selectivity. However, platinum catalysts have excellent selectivity, but have the disadvantages of a high price and a very low conversion.

A CrOx catalyst, which is a representative oxide catalyst, is a form in which $Cr^{6+}$ and $Cr^{3+}$ are stable, and most of the catalyst prepared by calcining at a high temperature is in the $Cr^{3+}$ state as $Cr_2O_3$, but some $Cr^{6+}$ is present. In the prepared catalyst (new catalyst), oxygen (generated from the lattice oxygen of the oxidation catalyst) generated while $Cr^{6+}$ is reduced to $Cr^{3+}$ at the initial stage of the reaction participates in the propane dehydrogenation reaction, thereby contributing to the production of $CO_2$ rather than propylene.

In the fixed bed reactor, initial $CO_2$ selectivity would not be a big problem when the residence time of the catalyst lengthened (high selectivity propylene is produced even a few seconds after the reaction).

However, since the residence time of the catalyst in the fluidized bed reactor is within 10 seconds, $CO_2$ production by the complete oxidation reaction of propane on a transition metal oxide catalyst becomes a big problem at the initial stage of the reaction, so that it is essential to control the level of oxidation of the transition metal in order to secure propylene selectivity. After all, in the case of the FPDH process using a fluidized bed reactor, the selectivity issue is very important because the reaction time is short.

Meanwhile, since the dehydrogenation reaction is an endothermic reaction, the supplied heat is increased as the reaction temperature is increased, so that reaction activity is increased. However, since the PDH reaction is also an equilibrium reaction, there is a limitation in increasing the conversion unless the produced hydrogen is removed.

The oxidative dehydrogenation of propane (ODHP) has been widely studied as a method for increasing the energy consumption and equilibrium conversion of such a direct dehydrogenation reaction. The reaction removes produced hydrogen in the form of water by additionally supplying oxygen in addition to propane as reactants. The advantage of the reaction is that the amount of energy consumption of dehydrogenation reaction can be reduced because the combustion reaction in which oxygen reacts is an exothermic reaction, and there is an effect of increasing the conversion. However, since oxygen is supplied as a reactant, there is a disadvantage in that the selectivity of propylene is lower than that of the direct dehydrogenation reaction.

SUMMARY

Thus, through continuous studies, the present inventors developed a new concept of catalyst which could solve problems in the related art, and allowed hydrogen to be converted into water by using oxygen inside the lattice of an oxide catalyst without the additional supply of oxygen, and thus, could increase the conversion while the decrease in selectivity, which is a disadvantage of an additional oxidative dehydrogenation of propane (ODHP), was suppressed. In this case, oxygen consumed in the catalyst lattice can be supplied by rapid recycling of a catalyst regeneration part and a reaction part in an FPDH process.

To solve the above problems, a catalyst for producing an olefin according to the present invention includes an oxygen carrier material and a dehydrogenation catalyst.

It is preferred that the oxygen carrier material includes oxygen in a lattice structure.

It is more preferred that the oxygen carrier material has an ABOx structure.

It is preferred that, in the ABOx structure, A or B is independently selected from the group consisting of sodium, magnesium, manganese, yttrium, zirconium, indium, antimony, cerium, tungsten, and bismuth.

More specifically, it is preferred that the oxygen carrier material is $Bi_2O_3$, $Sb_2O_4$, $In_2O_3$, $CeO_2$, $WO_x$, $ZrO_2$—$Y_2O_3$, $Na_2WO_4$ or $Mg_6MnO_8$, or a mixture thereof.

It is preferred that the dehydrogenation catalyst is an active metal oxide supported on a support.

It is preferred that the support includes alumina and an auxiliary support component.

It is more preferred that the auxiliary support component includes one or more selected from among zirconium, an alkali metal, and an alkaline earth metal.

It is more preferred that the active metal component includes one or more selected from among chromium, lanthanum, strontium, niobium, vanadium, gallium, cobalt, zirconium, tungsten, zinc, nickel-phosphorus, molybdenum carbide, palladium, platinum, platinum-tin, platinum-gallium, platinum-copper, platinum-manganese, an alkali metal, and an alkaline earth metal.

It is particularly preferred that the active metal component necessarily includes chromium.

It is particularly preferred that the active metal oxide is one or more selected from the group consisting of $NaCrO_x$, $KCrO_x$, $CaCrO_x$, $MgCrO_x$, $LaCrO_3$, $La_{0.8}Sr_{0.2}CrO_3$, $La_{0.7}Ca_{0.3}CrO_3$, $NbCrO_4$, and $SrCrO_4$.

A catalyst for producing an olefin according to the present invention allows hydrogen to be converted into water by using oxygen inside the lattice of an oxide catalyst without the additional supply of oxygen, and thus, the conversion can be increased while the decrease in selectivity, which is a disadvantage of an additional oxidative dehydrogenation reaction (ODHP), is suppressed.

DETAILED DESCRIPTION

To solve the above problems, a catalyst for producing an olefin according to the present invention includes an oxygen carrier material and a dehydrogenation catalyst.

It is preferred that the oxygen carrier material includes oxygen in a lattice structure.

It is more preferred that the oxygen carrier material has an ABOx structure.

It is preferred that the dehydrogenation catalyst is an active metal oxide supported on a support.

Hereinafter, preferred exemplary embodiments of the present invention will be described with reference to the accompanying drawings.

In describing these examples, the same names and symbols are used for the same configuration, and accordingly, the overlapping additional description will be omitted below. Scale ratios do not apply to the drawings referenced below.

Typically, there are various oxide catalysts as catalyst materials which can use oxygen inside the lattice. Among them, it is known that a perovskite structure allows oxygen inside the lattice to easily participate in the reaction. However, when the perovskite structure reacts directly with propane to perform the reaction, the disadvantage of low selectivity, such as the problem of ODHP in the related art, cannot be solved.

Figure 1:
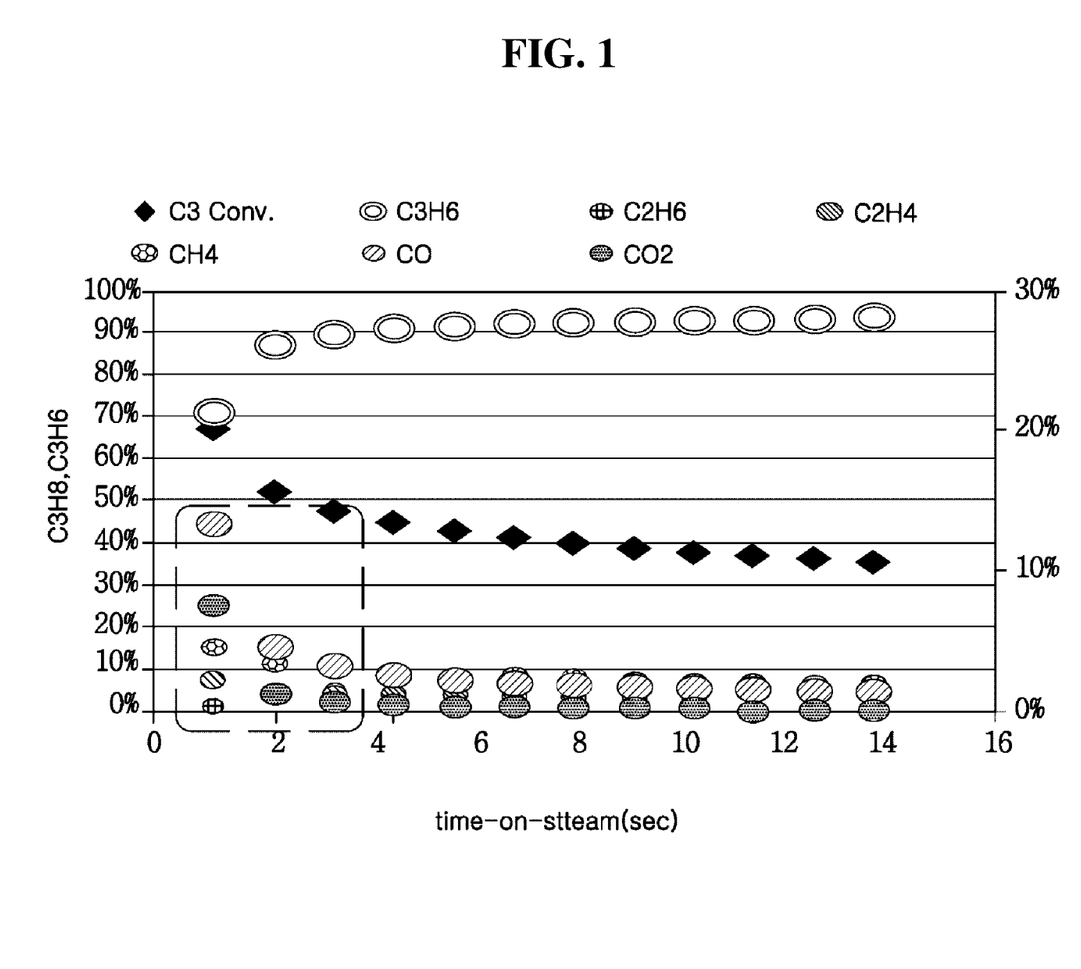
FIG. 1 schematically illustrates experimental results using perovskite structure catalysts as oxygen carrier materials.

As described above, in an FPDH process, the selectivity at the initial stage of the reaction is very important, and as a result of performing an experiment using a perovskite structure catalyst as an oxygen carrier material, there was a problem in that the selectivity of CO and $CO_2$ was still high at the initial stage of the reaction, as illustrated in FIG. 1.

In order to solve the problems, a catalyst for producing an olefin according to the present invention includes an oxygen carrier material and a dehydrogenation catalyst. It is preferred that the oxygen carrier material includes oxygen in a lattice structure.

Accordingly, the present invention can allow hydrogen generated by dehydrogenation catalysis to be converted into water by using oxygen inside the lattice of an oxide catalyst without the additional supply of oxygen.

Specifically, in the catalyst for producing an olefin according to the present invention, the oxygen carrier material and the dehydrogenation catalyst play different roles, respectively. The dehydrogenation catalyst contributes only to a reaction of producing propylene and hydrogen with propane, and the hydrogen produced thereafter reacts with oxygen present in the oxygen carrier material, and thus is selectively converted into water.

Accordingly, the dehydrogenation catalyst should have the highest selectivity for propylene and contribute only to the dehydrogenation reaction of propane.

Meanwhile, the oxygen carrier material is not reactive with propane or propylene, and should allow only hydrogen to be selectively reacted.

Accordingly, it is more preferred that the oxygen carrier material has an ABOx structure.

It is preferred that in the ABOx structure, A or B is independently selected from the group consisting of sodium, magnesium, manganese, yttrium, zirconium, indium, antimony, cerium, tungsten, and bismuth.

More specifically, it is preferred that the oxygen carrier material is $Bi_2O_3$, $Sb_2O_4$, $In_2O_3$, $CeO_2$, $WO_x$, $ZrO_2$—$Y_2O_3$, $Na_2WO_4$ or $Mg_6MnO_8$, or a mixture thereof.

Meanwhile, it is preferred that the dehydrogenation catalyst is an active metal oxide supported on a support.

It is preferred that the support includes alumina and an auxiliary support component.

It is more preferred that the auxiliary support component includes one or more selected from among zirconium, an alkali metal, and an alkaline earth metal. Lithium, sodium, potassium, and the like are possible as the alkali metal, and magnesium, and the like are possible as the alkaline earth metal, which will be obvious to those skilled in the art.

As the auxiliary support component, zirconium is particularly preferred, and it is preferred that the zirconium is present at a molar fraction of 0.01 to 0.1 (Zr:Al) with respect to aluminum in alumina.

The catalyst according to the present invention has improved durability due to the auxiliary support component, and a superior function of exciting the C—H bond of a paraffin raw material compared to the case where only alumina is used as the support. Thereby the hydrocarbon conversion and the olefin yield are excellent, and olefin selectivity is also improved. In particular, zirconium serves to improve the durability of an alumina support.

When the content of the auxiliary support component, particularly zirconium, is less than a molar ratio of 0.01 with respect to aluminum, the durability improvement effect feature does not appear, and when the content exceeds a molar ratio of 0.1, the surface area of the alumina support is sharply reduced, so that the active metal component supported cannot be polydispersed.

The alumina support preferably has a y to 0 phase at a preparation temperature of 550 to 850° C., which is equal to or higher than the dehydrogenation reaction temperature, and has a surface area of 80 to 300 m$^2$/g in this range.

When the support is prepared at a temperature lower than the dehydrogenation reaction temperature, thermal transformation of the catalyst may occur during the dehydrogenation reaction, and when the support is prepared at a temperature higher than 850° C., crystallization of the support results in a low catalyst surface area, which will interfere with the transfer of material for catalytic activity upon contact with the reactants.

It is more preferred that the active metal component includes one or more selected from among chromium, lanthanum, strontium, niobium, vanadium, gallium, cobalt, zirconium, tungsten, zinc, nickel-phosphorus, molybdenum carbide, palladium, platinum, platinum-tin, platinum-gallium, platinum-copper, platinum-manganese, an alkali metal, and an alkaline earth metal.

It is particularly preferred that the active metal component necessarily includes chromium, but the active metal component may also include vanadium, gallium, cobalt, zirconium, tungsten, zinc, niobium, nickel-phosphorus, molybdenum carbide, palladium, platinum, platinum-tin, platinum-gallium, platinum-copper, platinum-manganese, and the like as a non-chromium-based component.

It is particularly preferred that the active metal oxide is one or more selected from the group consisting of $NaCrO_X$, $KCrO_X$, $CaCrO_X$, $MgCrO_X$, $LaCrO_3$, $La_{0.8}Sr_{0.2}CrO_3$, $La_{0.7}Ca_{0.3}CrO_3$, $NbCrO_4$, and $SrCrO_4$.

Hereinafter, the present invention will be described in more detail through Preparation Examples and Examples.

PREPARATION EXAMPLES

1. Preparation of Support (Zr—Al$_2$O$_3$)

After 25 kg of water was added to 13.89 kg of Catapal B (alumina, sold by Sasol) and the resulting mixture was stirred for 30 minutes, 1.83 kg of ZrO(NO$_3$)$_2$ and 25 kg of water were mixed therewith, and the resulting mixture was stirred for an additional 2.5 hours. After spray drying (feed rate 0.56 g/min, atomizer 6000 rpm, inlet temperature 208° C., outlet temperature 125° C.), sieving (75 to 200 mm) was performed, and the product was calcined at 650° C. for 6 hours.

2. Preparation of Catalyst [(Based on 1% Cr) LaCrO$_3$/Zr—Al$_2$O$_3$]

In order to increase the dispersibility of a metal oxide, the metal oxide was prepared by dissolving a metal nitrate hydrate in a citric acid and ethylene glycol (EG) solution. After 22.2 g of La(NO$_3$)$_3$.6H$_2$O (lanthanum nitrate hexahydrate) was dissolved in 46 g of water and stirred for 30 minutes, the resulting solution was stirred while dissolving 20.52 g of Cr(NO$_3$)$_3$.9H$_2$O (chromium (III) nitrate nonahydrate) therein. 63.64 g of citric acid was added to the prepared aqueous solution of metal nitrate hydrate and stirred for 1 hour to dissolve all components, and then 18.724 g of ethylene glycol was added thereto and the resulting mixture was stirred for 1 hour. 0.65 g of the prepared solution was added to 1 g of the support (Zr—Al$_2$O$_3$) prepared in Preparation Example 1, impregnation was performed by incipient wetness impregnation, and the resulting product was dried at 120° C. for 15 hours, and then calcined at 850° C. for 10 hours.

<Reactivity Testing of Oxygen Carrier Material>

Figure 2:
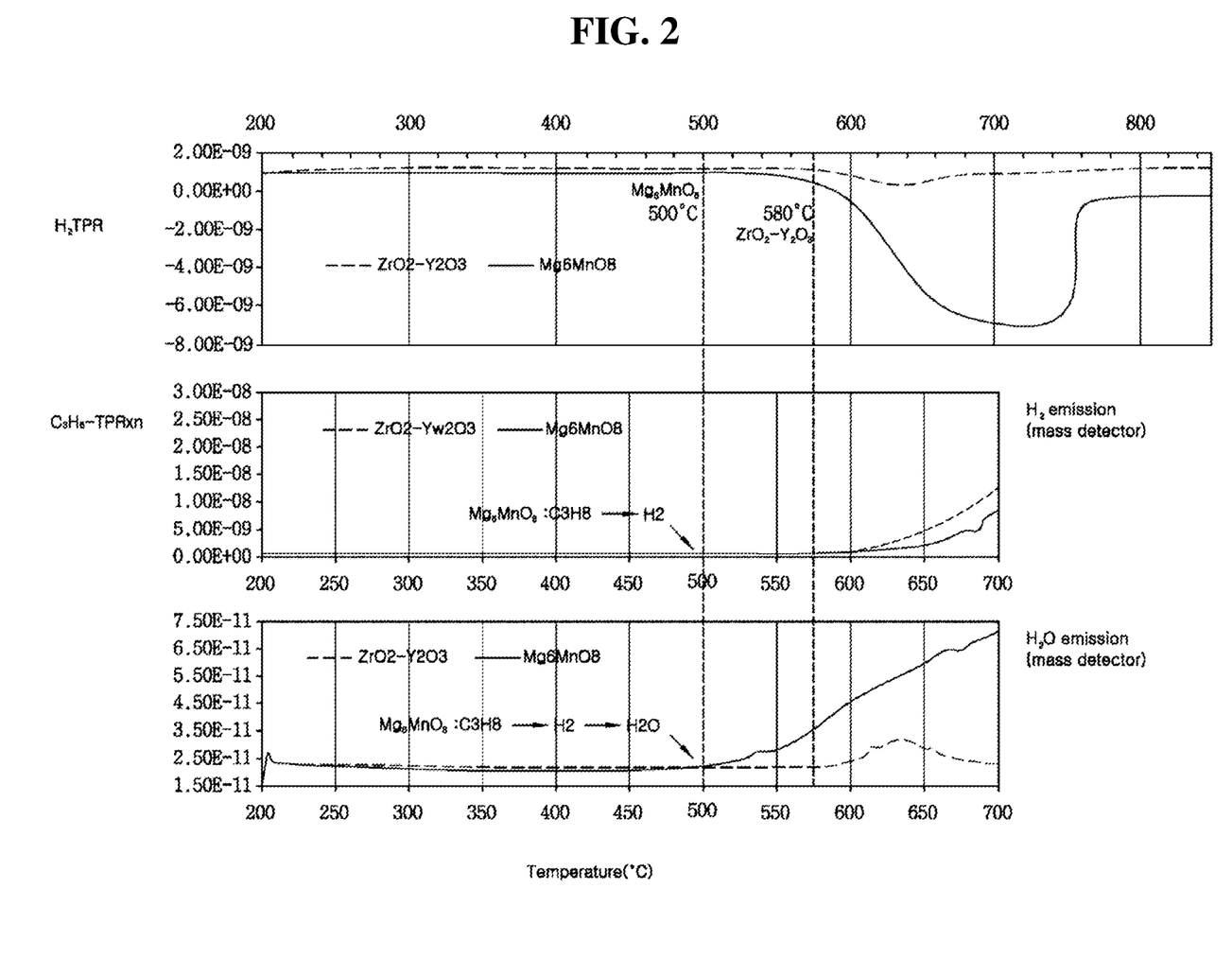
FIG. 2 schematically illustrates the reactivity test results of oxygen carrier materials.

H$_2$-temperature-programmed reduction (TPR) and C$_3$H$_8$-TPRxn experiments were performed to confirm the presence or absence of reactivity of the oxygen carrier material (OCM) to propane while selectively reacting with only hydrogen, and the results are schematically illustrated in FIG. 2.

<H$_2$-TPR Test Method>

The H$_2$-TPR experiment is a method for measuring the reducing power of a substance with respect to hydrogen, and was performed as follows. First, after 0.1 to 0.4 g of the oxygen carrier material was injected into a U-shaped reactor, and then oxidized at 650° C. in an air atmosphere for 1 hour, the temperature was lowered to 200° C. Thereafter, oxygen adsorbed onto the reactor and the catalyst was removed using a helium gas for 1 hour, and then a 10% H$_2$/Ar mixed gas was injected at a flow rate of 50 mL/min to detect the behavior of hydrogen consumption through a thermal conductivity detector (TCD) while increasing the temperature to 850° C. at a rate of 10° C./min.

<C$_3$H$_8$-TPRxn Test Method>

A propane-TPRxn experiment was performed to confirm the reactivity of the oxygen carrier material to propane. After 0.4 g of the oxygen carrier material was injected into a fixed bed-like circular reactor, the oxygen carrier material was oxidized at 640° C. in an air atmosphere for 1 hour, and then the temperature was lowered to 200° C. Thereafter, oxygen adsorbed onto the reactor and the catalyst were removed using a helium gas for 1 hour, and then the reactivity to propane was confirmed by injecting a 50% C$_3$H$_8$/N$_2$ mixed gas at a flow rate of 110 mL/min and increasing the temperature to 700° C. at a rate of 10° C./min.

As a result of the experiments, when reviewing the H$_2$-TPR result in order to confirm the selective reactivity of the two materials of ZrO$_2$—Y$_2$O$_3$ and Mg$_6$MnO$_8$ materials to hydrogen, through the fact that Mg$_6$MnO$_8$ decreases the amount of hydrogen from 500° C. and the ZrO$_2$—Y$_2$O$_3$ material decreases the amount of hydrogen from 580° C., it can be seen that the reaction starts with lattice oxygen in the catalyst from 500° C. and 580° C., respectively.

Further, in order to confirm the reactivity of ZrO$_2$—Y$_2$O$_3$ to propane, the temperature at which hydrogen and water were simultaneously produced was confirmed by performing a propane TPR reaction. First, when reviewing a graph of hydrogen production (hydrogen is detected by a mass detector only when propane reacts), it was confirmed that ZrO$_2$—Y$_2$O$_3$ did not react with propane up to 600° C. It can be seen that after 600° C., hydrogen produced from propane reacted by heat is emitted. As seen in the $H_2O$ emission graph in FIG. 2, it could be confirmed that the hydrogen produced by heat reacted with the lattice oxygen in $ZrO_2$—$Y_2O_3$ to be converted into water.

Meanwhile, in order to confirm the reactivity of the $Mg_6MnO_8$ material to propane, the propane TPR reaction and hydrogen and water were detected. In the same manner as $ZrO_2$—$Y_2O_3$ above, it appears in the $H_2$ emission graph that the material does not react with propane, but when reviewing the bottom $H_2O$ emission graph in FIG. 2, considering that water is produced from 500° C., the material reacts with propane from 500° C. to produce hydrogen, but the material appears to show a big peak from 500° C. in the $H_2O$ emission, unlike the $H_2$ emission graph, because hydrogen is rapidly converted into water due to very abundant lattice oxygen.

In conclusion, although it is determined that $ZrO_2$—$Y_2O_3$ is not reactive with propane up to 600° C., so that $ZrO_2$—$Y_2O_3$ can be applied in a wide temperature range, the amount of lattice oxygen is relatively small, and the $Mg_6MnO_8$ material contains a very abundant amount of lattice oxygen, on the other hand, the $Mg_6MnO_8$ material serves as a PDH catalyst at a reaction temperature of 500° C. or more, so that it is determined that it is difficult to selectively remove hydrogen. Accordingly, studies on increasing the reduction temperature for hydrogen and propane were further performed by introducing an additional material ($Na_2WO_4$) into the $Mg_6MnO_8$ material.

3. Preparation of Oxygen Carrier Material ($Na_2WO_4$—$Mg_6MnO_8$)

After 2.45 g of $Mn(NO_3)_2$ (manganese (II) nitrate) was dissolved in 4.5 g of water and the resulting solution was stirred for 30 minutes, 5 g of magnesium oxide (MgO) was added thereto and impregnated by an impregnation method to prepare a slurry. After the prepared slurry was dried at 120° C. for 15 hours, lumps were crushed by a mortar and filtered by a sieve to recover a catalyst having a size smaller than 200 µm. The nitrate group was pyrolyzed by calcining the recovered catalyst at 200° C. for 4 hours. Thereafter, an aqueous tungsten oxide solution of 0.61 g of $Na_2WO_4.2H_2O$ (sodium tungstate dihydrate) dissolved in 4 g of water was prepared, the calcined catalyst was added thereto, and the resulting mixture was impregnated by an impregnation method. The impregnated catalyst was dried at 120° C. for 15 hours, and then calcined at 450° C. for 3 hours and at 850° C. for 8 hours.

<Reactivity Testing of Oxygen Carrier Material>

Figure 3:
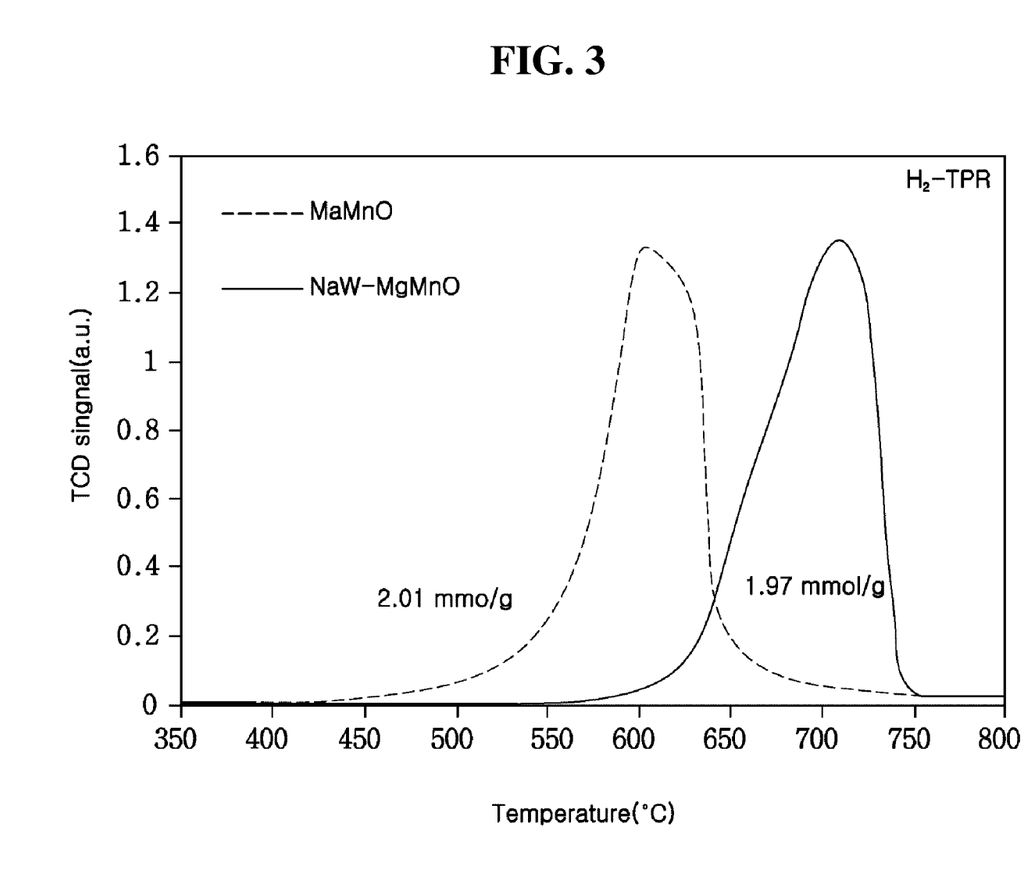
FIG. 3 schematically illustrates hydrogen reduction temperatures of other oxygen carrier materials.

As a result of confirming the hydrogen reducing power of the prepared oxygen carrier material ($Na_2WO_4$—$Mg_6MnO_8$) through the $H_2$-TPR experiment, as illustrated in FIG. 3, it was confirmed that the reduction temperature after adding $Na_2WO_4$ was increased by about 100° C. and the amount of hydrogen reduced was hardly changed.

Figure 4:
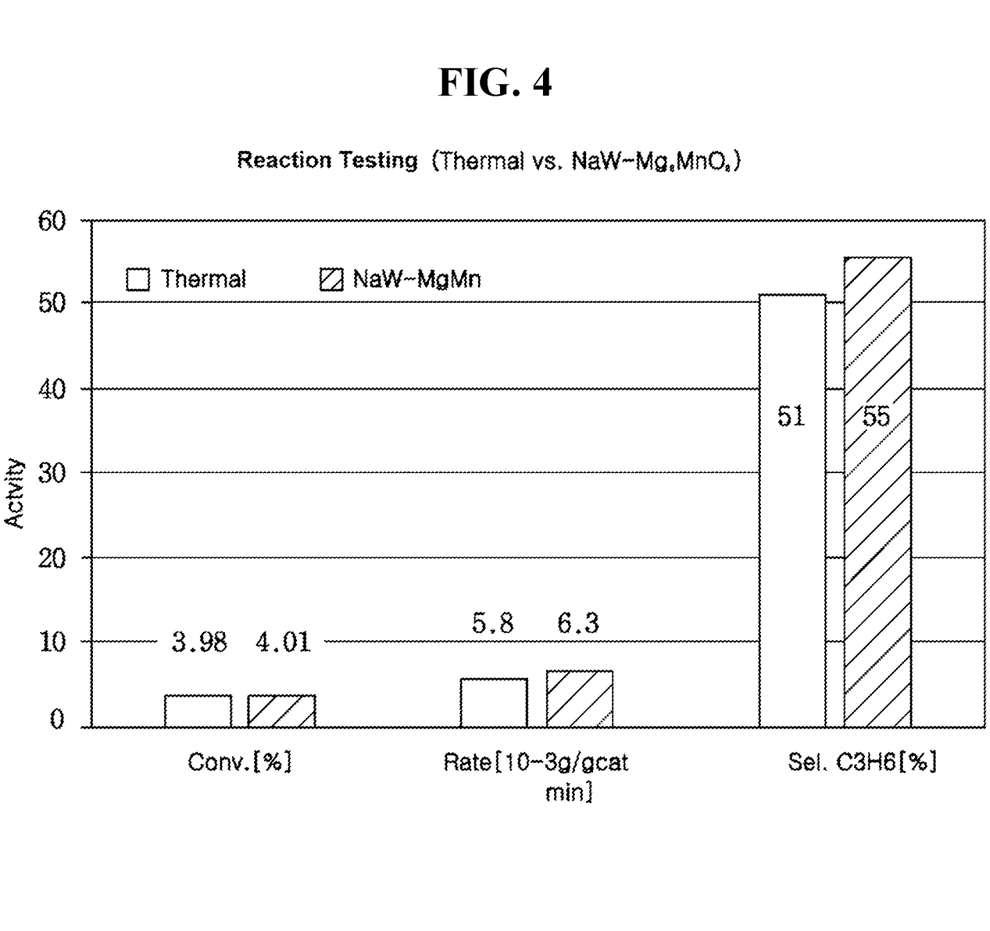
FIG. 4 schematically illustrates the reactivity test results of the oxygen carrier material of FIG. 3.

Thereafter, as a result of comparison with the pyrolysis reaction under the condition of WHSV: 17.3 $h^{-1}$ at 640° C. in order to confirm the reactivity of the prepared oxygen carrier material to propane, as illustrated in FIG. 4, it was confirmed that the propane conversion and selectivity were similar to those of the pyrolysis reaction experiment without a catalytic material.

In conclusion, it is determined that an excellent oxygen carrier material having no reactivity with propane while increasing the reduction temperature for hydrogen was synthesized.

Figure 5:
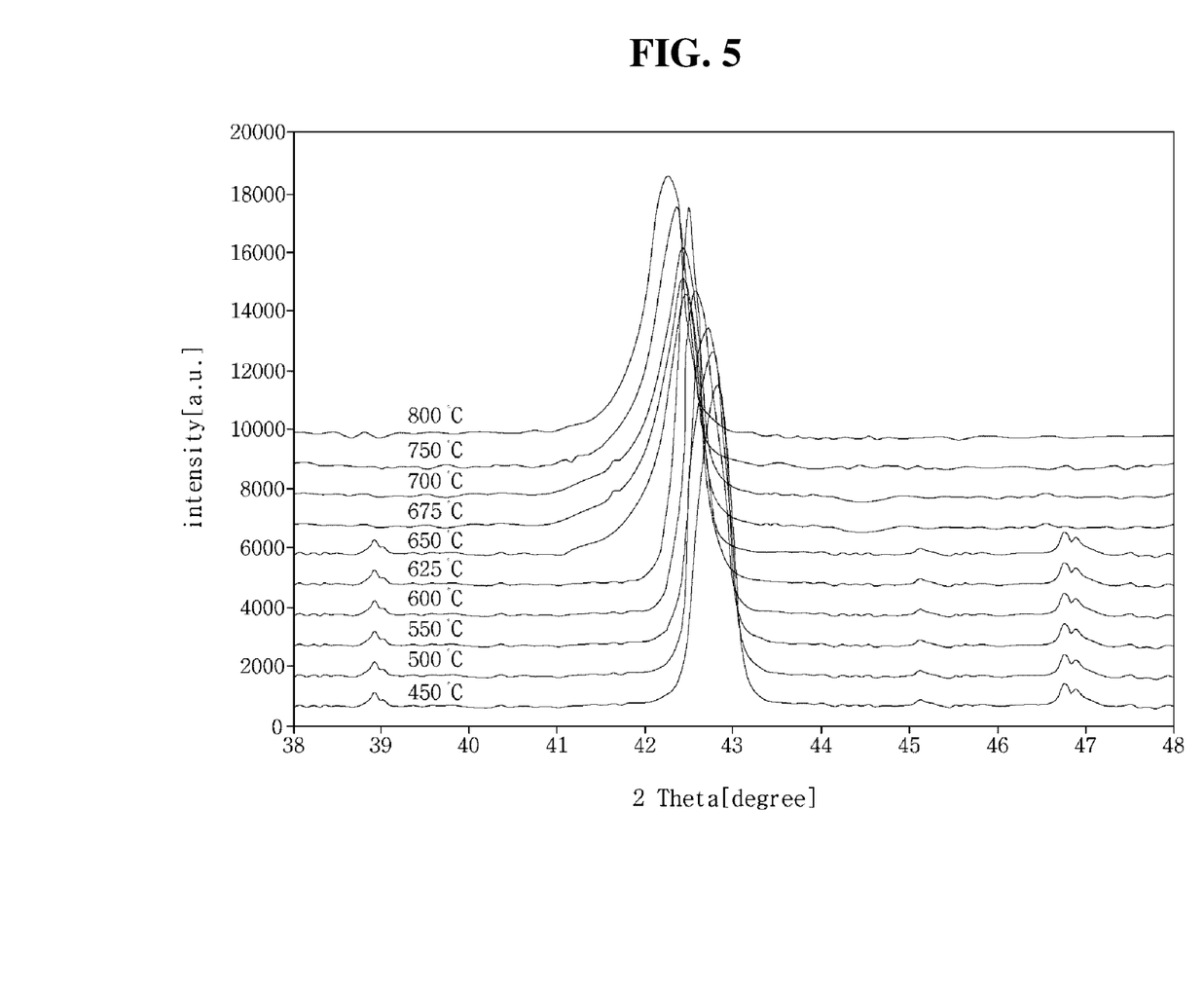
FIG. 5 schematically illustrates the lattice oxygen utilization phenomenon of the oxygen carrier material of FIG. 3 observed by XRD.

In order to observe the utilization phenomenon of lattice oxygen of the prepared oxygen carrier material, the peak of a crystal plane was observed while injecting a 10% $H_2N_2$ mixed gas in a temperature range of 300 to 800° C. using an In-situ XRD device. As a result, it was observed that all peaks moved to a lower angle around 600° C., and it was shown in FIG. 5 that a peak at 42.9°, which is the main peak, moved to a lower angle of 42.6°. This is because oxygen inside the lattice escapes to widen the distance between planes (d-spacing) while reacting with hydrogen, and is a result of confirming that the lattice oxygen of the prepared material is used by hydrogen.

<PDH and PDH+OCM Reactivity Comparison Experiment>

After 0.4 g of a PDH catalyst ($LaCrO_3$/Zr—$Al_2O_3$) and 0.1 g of an oxygen carrier substance ($Mg_6MnO_8$) were physically mixed, the reactivities were compared by performing a propane TPRxn experiment. Reactivity results according to temperature were obtained after feeding propane at 110 mL/min while increasing the temperature from 200° C. to 700° C. at a rate of 10° C. per minute, and confirming propylene selectivity and a hydrogen production rate by GC and a mass detector, respectively and are schematically illustrated in FIG. 6, compared to the case where only PDH is used.

Figure 6:
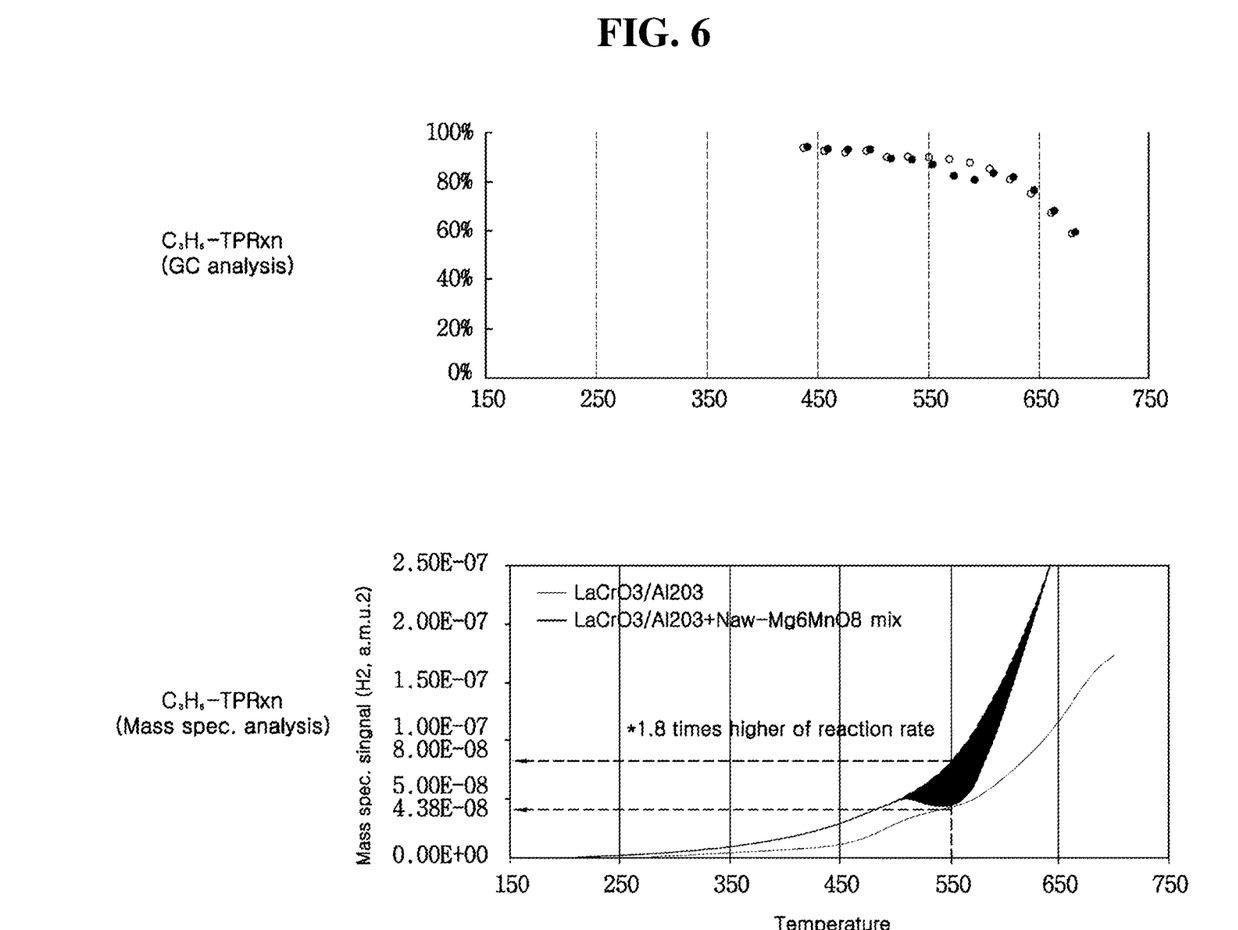
FIG. 6 schematically illustrates the reactivity test results using the oxygen carrier materials in combination compared to the case where only a dehydrogenation catalyst is used.

As illustrated in FIG. 6, the red color is data obtained by mixing a PDH catalyst with OCM, and the blue color is data obtained when only the PDH catalyst is present. It was observed that the selectivity showed a slight decrease in the temperature interval at which the OCM material began to participate in the reaction of converting hydrogen into water, but then recovered again. In addition, it was confirmed that the production rate of hydrogen, that is, the overall reaction rate, proceeded at about 2-fold higher after the introduction of OCM, meaning that OCM very effectively converts the hydrogen produced by the PDH catalyst into water, resulting in a faster overall reaction rate.

Figure 7:
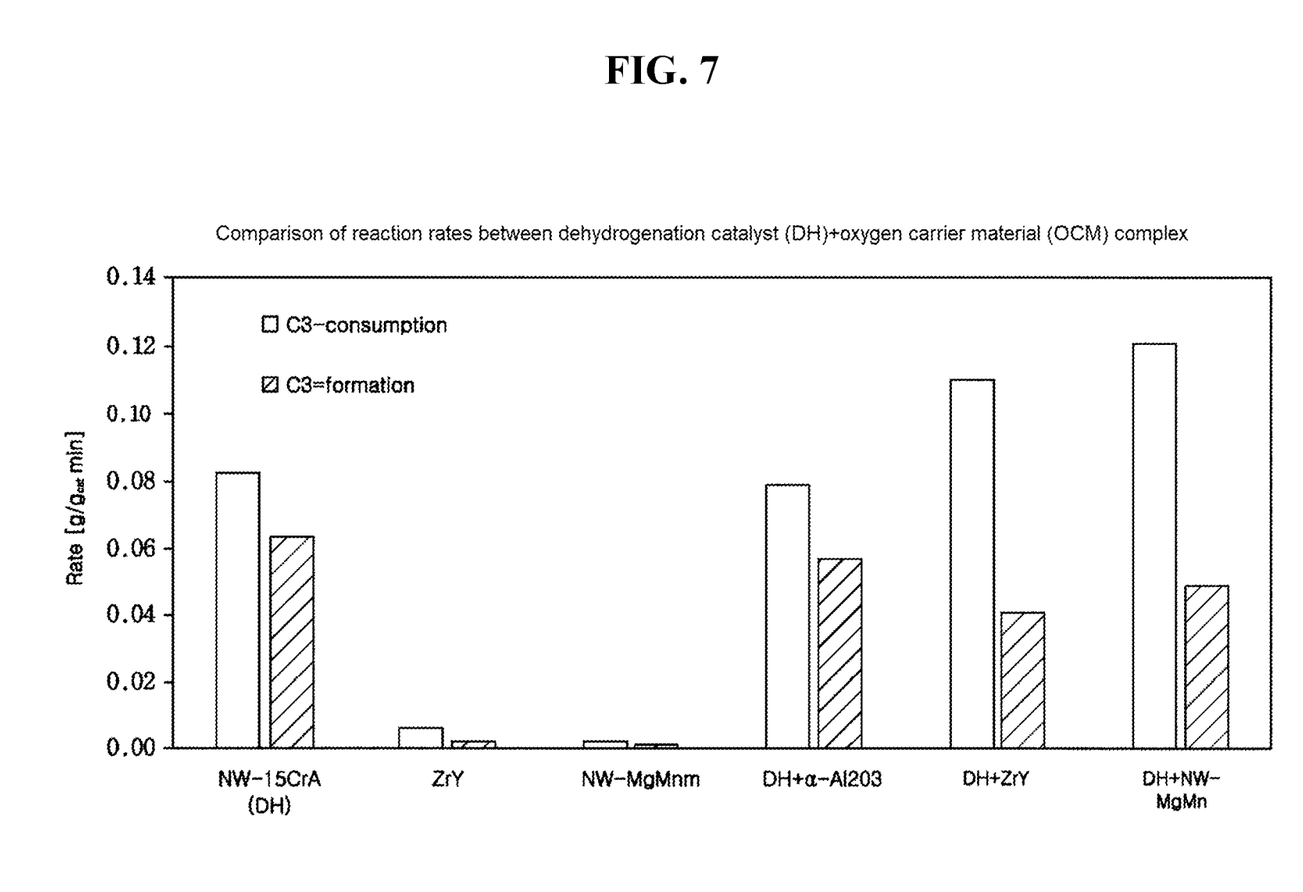
FIG. 7 schematically illustrates the reaction rate of a complex using a dehydrogenation catalyst and an oxygen carrier material.

FIG. 7 is a result illustrating the activities of a dehydrogenation catalyst (DH: 0.25% $Na_2WO_4$-15% Cr/Zr-$Al_2O_3$) and a dehydrogenation catalyst/oxygen carrier material (OCM) complex in the propane dehydrogenation reaction. As a result of performing an experiment under the conditions of a reaction temperature of 560° C., 50% propane/nitrogen flow, and WHSV17.3 $h^{-1}$, it was confirmed that there was almost no reaction activity with the OCM material alone, and a propane consumption/propylene production rate at the pyrolysis reaction level was exhibited. When observing the results of the alpha-alumina ($\alpha$-$Al_2O_3$)+DH complex, which is a non-oxygen carrier material (non-OCM) which does not contribute to the propane dehydrogenation reaction and oxygen transfer reaction, the propane consumption/propylene production rate is decreased by about 5%. In comparison, the oxygen carrier materials $ZrO_2$-$Y_2O_3$ (ZrY) and $Na_2WO_4$-$Mg_6MnO_8$ (NW-MgMn) formed a complex with the main catalyst and showed an increase in propane consumption rate of 33% and 46%, respectively. This is due to the properties of an oxygen carrier, which selectively converts the produced hydrogen into water to make the equilibrium reaction a more forward reaction. However, a result that the propylene production rate was decreased by 48% and 38%, respectively, was exhibited, leading to a determination that the case where the supply of lattice oxygen not only selectively converted hydrogen, but also formed a complex with a dehydrogenation catalyst was involved in the secondary reaction of the produced propylene to produce a side reaction.

Even though the exemplary embodiments of the present invention have been described in detail, the scope of rights of the present invention is not limited thereto, and it will be obvious to a person with ordinary skill in the art that various modifications and alterations are possible without departing from the technical spirit of the present invention described in the claims.

The present invention relates to a catalyst for producing an olefin with improved selectivity and conversion, including an oxygen carrier material.

The invention claimed is:

1. A catalyst for producing an olefin, comprising an oxygen carrier material and a dehydrogenation catalyst,
   wherein the dehydrogenation catalyst is $Na_2WO_4$-$Cr/Zr$-$Al_2O_3$ or $LaCrO_3/Zr$-$Al_2O_3$;
   wherein the oxygen carrier material comprises $ZrO_2$-$Y_2O_3$ $Mg_6MnO_8$; or $Na_2WO_4$-$Mg_6MnO_8$ when the dehydrogenation catalyst is $Na_2WO_4$-$Cr/Zr$-$Al_2O_3$ and
   wherein the oxygen carrier material comprises $ZrO_2$-$Y_2O_3$ when the dehydrogenation catalyst is $LaCrO_3/Zr$-$Al_2O_3$.

* * * * *